United States Patent [19]

Collins et al.

[11] Patent Number: 4,752,566

[45] Date of Patent: Jun. 21, 1988

[54] DISPLACEMENT POLYNUCLEOTIDE METHOD AND REAGENT COMPLEX EMPLOYING LABELED PROBE POLYNUCLEOTIDE

[75] Inventors: Mary Collins, Natick; Joseph P. Dougherty, Somerville, both of Mass.

[73] Assignee: Genetics Institute, Inc., Cambridge, Mass.

[21] Appl. No.: 809,992

[22] Filed: Dec. 17, 1985

[51] Int. Cl.[4] .................... C12Q 1/68; G01N 33/566
[52] U.S. Cl. .......................... 435/6; 435/1; 436/501; 536/26; 536/27; 536/28; 935/77; 935/78
[58] Field of Search .......................... 435/6, 7, 77, 78; 436/501; 536/28, 29, 27, 26

[56] References Cited

U.S. PATENT DOCUMENTS 4,205,952 6/1980 Cais ........................................ 436/518
4,563,417 1/1986 Albarella et al. ...................... 935/78

FOREIGN PATENT DOCUMENTS 2139349 7/1984 United Kingdom .................. 935/77

OTHER PUBLICATIONS

Green, C., et al, Nucleic Acids Research, 9, No. 8: 1905-1918, 1981.

Primary Examiner—Robert J. Warden
Assistant Examiner—Jack Spiegel
Attorney, Agent, or Firm—Bruce M. Eisen; Mary E. Bak; Brian P. O'Shaughnessy

[57] ABSTRACT

A method for determining the presence and amount of a predetermined target nucleotide sequence in a biological sample is provided. The method employs a reagent complex which consists of a labeled probe polynucleotide having a target binding region and a second polynucleotide bound to the labeled probe in a second polynucleotide binding region thereof. The second binding region is at least partially coextensive with the target binding region. This reagent complex is contacted with a sample under conditions in which the target sequence binds to the labeled probe, displacing the second polynucleotide. Labeled probe/target hybrids are separated from intact reagent complexes and the presence and amount of these hybrids are determined.

5 Claims, 2 Drawing Sheets

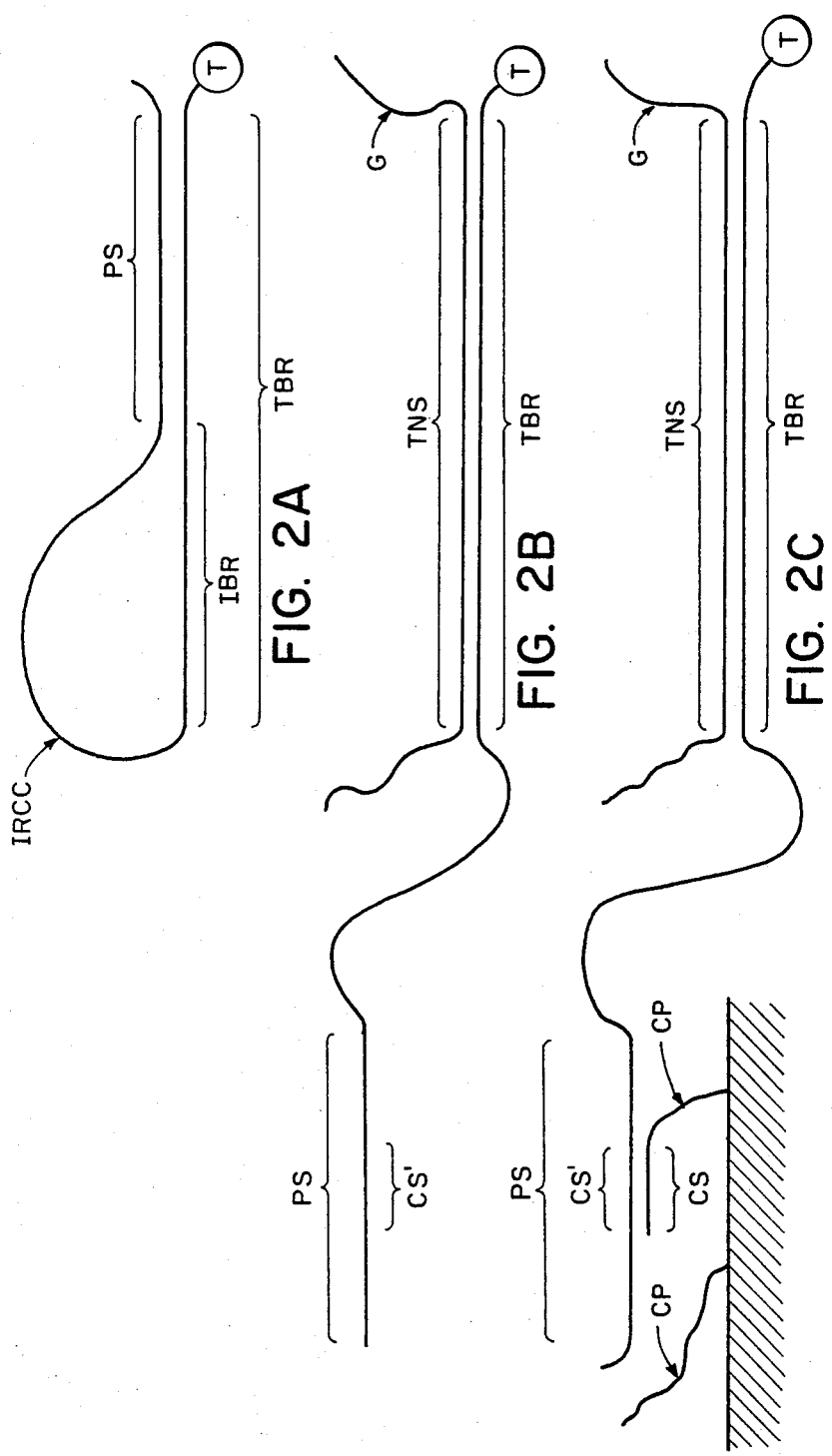

DISPLACEMENT POLYNUCLEOTIDE METHOD AND REAGENT COMPLEX EMPLOYING LABELED PROBE POLYNUCLEOTIDE

BACKGROUND OF THE INVENTION

The present invention relates to a diagnostic assay method for detecting the presence of a target nucleotide sequence (either DNA or RNA) in a biological sample, and to a polynucleotide reagent complex therefor.

Conventional methods for detecting the presence of a particular polynucleotide in a biological sample typically involve immobilization of nucleic acid of the sample on a surface as the initial step. Once the sample is immobilized, a probe polynucleotide strand, itself labeled or subsequently labeled (see EPA No. 63,879 (1982)) is incubated with the immobilized sample so as to bind to the immobilized sample by purine/pyrimidine base sequence-specific complementary base pairing when the immobilized sample contains the target nucleotide sequence. After washing off the labeled probe which has not so hybridized, the presence or absence of label on the support is then determined. Techniques for this determination include exposure of a photographic film, liquid scintillation counting, and fluorescence microscopy. With subsequent labeling (e.g., by avidin-enzyme conjugate binding to biotin on the probe) various enzyme-amplified read-outs may be used.

Other known methods involve solution hybridization of a labeled probe polynucleotide to the target nucleotide sequence of single-stranded sample polynucleotides, followed by separation and detection of labeled probe/sample polynucleotide hybrids. See PCT WO No. 84/02721 of Kohne (1984). Another assay involving solution hybridization of a labeled probe to the target nucleotide sequence is disclosed in co-pending U.S. Ser. No. 790,671 of Ellwood, et al., filed Oct. 23, 1985.

A group of inventors including M. Collins have filed a series of applications describing a displacement polynucleotide assay, reagent complexes therefor and kits for such assays including such reagent complexes. See, e.g., U.S. Ser. No. 607,885 of Diamond, et al, filed May 7, 1984, 684,305 of Collins, et al, filed Dec. 20, 1984 and U.S. Ser. No. 684,308 of Williams, et al filed Dec. 20, 1984; also see EPA No. 164,876 to be published Dec. 18, 1985, and EPA No. 167,238, to be published Jan. 8, 1986. Such assays and reagent complexes all employ:

(a) a target binding region of the probe polynucleotide which is capable of complementary base pair binding to the target nucleotide sequence to be detected, and
(b) a labeled polynucleotide bound in the reagent complex to the probe, generally by complementary base pair binding to a portion of the target binding region.

While in such system, the probe and labeled polynucleotide are generally separate molecules, certain embodiments provide that they may be segments of a single polynucleotide strand, whose preferred means of manufacture is described in U.S. Ser. No. 729,504 of Fritsch, et al. In any event, such assay methods all involve determining the displaced labeled polynucleotide or labeled polynucleotide which is not displaced.

U.S. Ser. No. 777,657 of Fritsch and Williams, filed Sept. 19, 1985, describes reagent complexes with a labeled probe polynucleotide and a second polynucleotide bound thereto in at least a portion of the target binding region. The target binding region contains a half restriction site and the second polynucleotide has at least one mismatch opposite to the half restriction site. The target nucleotide sequence displaces the second polynucleotide from the target binding region and forms an endonuclease cleavage site where the mismatch had previously been. Enzymatic cleavage of such endonuclease cleavage site (but not intact reagent complexes) is followed by separation of labeled cleavage fragments from intact reagent complex, normally by employing an immobilized or immobilizable probe.

BRIEF DESCRIPTION OF THE INVENTION

The present invention employs a labeled probe polynucleotide, but permits the manipulative simplicity of the displacement assays of U.S.S.N. 607,885 and its progeny. The present invention provides a method for determining the presence of a predetermined target nucleotide sequence in the nucleic acid of a biological sample which comprises the steps:

(a) providing a reagent complex of (i) of labeled probe polynucleotide which is capable of base pair binding via hydrogen bonds of purine/pyrimidine bases to the target nucleotide sequence, and (ii) a second polynucleotide which is bound by base pair binding via hydrogen bonds of purine/pyrimidine base pairs to the labeled probe polynucleotide in a region of the labeled probe polynucleotide at least partially coextensive with the region in which the labeled probe polynucleotide is capable of binding to the target nucleotide sequence;

(b) contacting the reagent complex with a sample under conditions in which the target nucleotide sequence, if present, binds to the labeled probe polynucleotide and displaces second polynucleotide from the labeled probe polynucleotide;

(c) separating labeled probe polynucleotides from which second polynucleotide have been displaced from intact reagent complex; and (d) determining the presence and/or amount of labeled probe polynucleotides which have been separated.

The present invention also provides a diagnostic reagent for determining the presence of a predetermined target nucleotide sequence in the nucleic acid of a biological sample comprising:

(i) a labeled probe polynucleotide which is capable of base pair binding via hydrogen bonds of purine/pyrimidine base pairs to the target nucleotide sequence, and (ii) an immobilized or immobilizable second polynucleotide which is bound by base pair binding via hydrogen bonds of purine/pyrimidine base pairs to the labeled probe polynucleotide in a region of the labeled probe polynucleotide at least partially coextensive with the region in which the labeled probe polynucleotide is capable of base pair binding to the target nucleotide sequence;

the potential base pair binding between the target nucleotide sequence and the labeled probe polynucleotide being capable of displacing the second polynucleotide from the labeled probe polynucleotide.

The present invention also provides a reagent complex construct for determining the presence of a predetermined target nucleotide sequence in the nucleic acid of a biological sample which comprises:

(a) a polynucleotide strand having:
  (i) a target binding region segment which is capable of base pair binding via hydrogen bonds of purine/pyrimidine bases to the target nucleotide sequence, and
  (ii) a pairing segment which is bound by base pair binding via hydrogen bonds of purine/pyrimidine base pairs to a portion of the target binding region segment; and
(b) a detectable tag which is within or adjacent to the target binding region segment.

DETAILED DESCRIPTION OF THE INVENTION

Figure 1A:
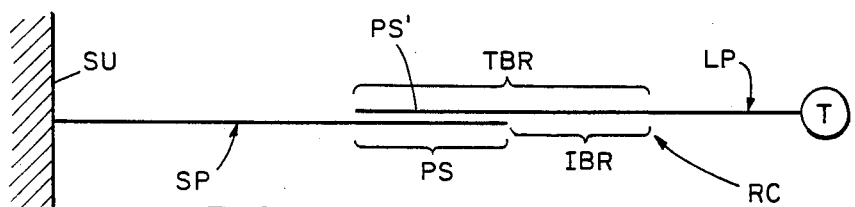

In this application the following terms are used based on their generally accepted meanings in the field of molecular biology:

Polynucleotide or Polynucleotide Strand refers to a linear polymeric structure of pentose sugars (generally ribose or deoxyribose) linked to each other by 3',5'-phosphodiester linkages, and linked by carbon-nitrogen bonds at the 1-carbon of the sugar to pendant purine or pyrimidine bases such as, but not limited to, uracil (linked naturally to ribose only as rU), thymine (linked naturally to deoxyribose only as dT), cytosine (dC or rC), adenine (dA or rA) and guanine (dG or rG). Polynucleotides thus include strands of deoxyribonucleic acid (DNA) and strands of ribonucleic acid (RNA).

The ends of such Polynucleotide Strands are referred to as the Five Prime (5') end, where the 5-carbon of the pentose is not linked to another pentose (but may bear hydroxyl, monophosphate or other natural or synthetic moieties), and the Three Prime (3') end, where the 3-carbon of the pentose is not linked to another pentose (but may similarly bear hydroxyl, monophosphate or other natural or synthetic moieties).

Complementary Base Pairing or Purine/Pyrimidine Base Pairing refers to the hydrogen bonding between opposite bases pendant on two antiparallel Polynucleotide Strands, which is most energetically favorable for natural DNA when dG is opposite dC and dA is opposite dT. Bases other than the five naturally-prevalent ones also have preferential pairing: for example, 5-methylcytosine binds preferentially to guanine. For illustrative purposes, this pairing is shown in many of the Figures by parallel straight lines with complementary strands directed in antiparallel directions (in the 5' to 3' sense). It should be appreciated, however, that the actual geometry of double-stranded segments will normally be helical (the well-known double helix) of various pitches.

Hybridization is used herein to refer to admixing two Polynucleotides under conditions conducive to the formation of double-stranded structures, with Complementary Base Pairing causing such double stranded structures to form where complementary sequences or nearly complementary sequences are present.

The basic components of the method of the invention are a labeled probe polynucleotide (sometimes called herein the probe or labeled probe), a second polynucleotide and the biological sample containing nucleic acid, a portion of which is sometimes called herein the target polynucleotide or target nucleotide sequence. A sample may or may not contain a target nucleotide sequence. In some cases a volume excluding polymer such as a polyether compound is also provided. In some cases a support is also provided, either to which the reagent complex is immobilized via the second polynucleotide or in other cases as a part of the separation step that follows displacement. In practicing the method, additional reagents or equipment are frequently required for readout; the term readout refers to the direct or indirect detection of labeled probe polynucleotide in one or more phases of separated reaction materials, and especially in a liquid phase by virtue of displacement of the reagent complex and separation of labeled probe polynucleotide from which second polynucleotide has been displaced from a solid phase containing displaced second polynucleotides and intact reagent complexes.

In the practice of the present invention, the probe can be a linear or circular polynucleotide capable of binding specifically through complementary base pairing in at least one region of its purine/pyrimidine base sequence to specific target nucleotide sequences of a sample. This binding may be between DNA and RNA, between DNA and DNA or between RNA and RNA. Accordingly, the probe may either be DNA or RNA. As discussed more fully below, it is generally only a specific region of the probe which binds selectively to the target nucleotide sequence. Other regions of the probe may be of various naturally occurring or synthesized sequences which do not participate in the hybridization reaction with the target nucleotide sequence, but which may play an important role in the present invention, e.g., by serving as a site for attachment to a label or by providing some degree of separation between the label and the region to which the target nucleotide sequence binds, if desired.

Referring to the region of the probe to which the target nucleotide will specifically bind, called herein the target binding region (TBR in the Figures), the binding may be (and preferably is) perfect, in the sense that each nucleotide in the probe sequence finds its correct complementary binding partner (e.g., dA to dT) in the target nucleotide sequence, or may contain some mismatches. At least one portion of the target binding region of the probe is preferably single-stranded in the reagent complex, i.e., it is not complementary to second polynucleotide sequences nor self-complementary; this single-stranded region is sometimes called herein the initial binding region (IBR in the Figures) because the target nucleotide sequence can bind to this region of bases without displacing any of the second polynucleotide. Such initial binding region of the probe is at least fifteen bases in length, and is preferably at least fifty bases in length. The overall target binding region includes the initial binding region and most or (preferably) all of the second polynucleotide binding region (PS' in the Figures). The length of the overall target binding region is not independently critical, but rather can be considered as a function or sum of the preferred or more preferred lengths of the IBR and PS' portions. Base lengths of the initial binding region of the probe above five hundred are generally not required, but are not significantly disadvantageous in most cases. A suitable lower limit on the length of this region of base pairing for clinical laboratory applications is somewhat dependent upon base sequence of the target binding region of the probe and base composition and other physical factors described below, and especially upon the conditions for intended hybridization, kinetics of hybridization and the readout system employed. The second polynucleotide binding region may be at least 15 nucleotides in length, but is preferably between 20 to about 1000 nucleotide in length. The portion of the target binding region that is not part of the second polynucleotide binding region may be at least about 100 nucleotides in length, and is preferably at least the same length as the second polynucleotide binding region. In a preferred embodiment of the method of the invention, the labeled probe polynucleotide contains a target binding region capable of base pair binding to a sample target nucleotide sequence and contains a second polynucleotide binding region bound by purine/pyrimidine base pairing to the second polynucleotide of at least about 15 nucleotides. At least some of the nucleotides of the second polynucleotide region are included in the target binding region and no more than about 15 nucleotides of the second polynucleotide binding region are outside the target binding region.

In the present invention, unlike many of the embodiments specifically disclosed in U.S. Ser. No. 607,885, the probe also contains a detectable tag.

One or more tags may be located (using conventional techniques) at one of several points along the labeled probe polynucleotide (especially if the tag is a radionuclide or biotin or the like), only at one end or only at one specific internal location on the labeled polynucleotide (e.g., at a purine or pyrimidine base not involved in base pairing to the second polynucleotide). Provided that there is at least one region of the labeled probe polynucleotide outside the target binding region, the tag is preferably present or concentrated on or within such region. Directly detectable tags which may be used include radionuclides (especially phosphorus-32, sulfur-35, carbon-14 or iodine-125 labeled nucleotides), fluorescent compounds (such as fluorescein or rhodamine derivatives attached to the free end of a labeled probe polynucleotide or to one or more of the bases of a labeled probe polynucleotide) or moieties directly detectable by other means (including being cleaved off) such as the moiety nitrophenol detectable colorimetrically or otherwise. Indirectly detectable tags include those modifications that can serve as antigenic determinants, affinity ligands, antigens or antibodies recognizable through immunochemical or other affinity reactions such as described in EPA No. 63,879, WO No. 83/02277 and EPA No. 97,373, and exemplified by biotinated nucleotides present in or added onto the labeled probe polynucleotide (such as by the enzyme terminal deoxynucleotidyl transferase which will add multiple nucleotides at the 3' end of the labeled polynucleotide in the absence of a template strand). Other indirect tags include enzymes attached to a labeled probe polynucleotide (especially at a free end remote from the target binding region) whose presence can be determined after displacement and separation steps of the embodied method by addition of the substrate for the enzyme and quantification of either the enzymatic substrate or, preferably, the enzymatic reaction product. Similarly, the tag may be an apoenzyme, coenzyme, enzymatic modifier, enzymatic cofactors or the like, with the other necessary reagents usually added after displacement and separation, along with the appropriate enzymatic substrate. Of course, if the enzymatic reaction cannot occur with all but one component present (e.g., the substrate), then these other reagents may be present in solution during the contacting (displacement) step (b).

In addition to such conventional tags, the ribonucleotide segment tags of U.S. Ser. No. 729,502 and 729,503 of Vary, et al, each filed May 2, 1985, may also be used. Thus, for example, a poly(riboadenosine) segment (sometimes called herein poly A segment or tail) may be formed on the 3' end of a DNA portion of the probe, which DNA portion includes the target binding region. After displacement and separation, such polyA segment can be digested with polynucleotide phosphorylase (PNP) to riboadenosine diphosphate (ADP), which can then be phosphorylated by phosphoenol pyruvate in the presence of pyruvate kinase to ATP. The ATP so-formed can then be detected (e.g., with luciferin/luciferase) as an amplified signal indicative of the number of such labeled probe polynucleotides so separated.

Multiple detectable tags can be added in manufacturing the labeled probe polynucleotide by enzymes such as terminal deoxynucleotidyl transferase, DNA ligase, polynucleotide phosphorylase, etc. Multiple labeled probe polynucleotides, each containing a signalling moiety or detectable tag, can also be used. One form of attachment of an enzyme to the labeled probe polynucleotide is via affinity reagents, e.g., streptavidin to biotin. Such a binding form can be used in various embodiments, for example wherein the complex is prepared by hybridizing a biotin-labeled polynucleotide to the probe and then binding a streptavidin-enzyme conjugate to the biotin prior to the contacting (displacement) step (b), described above. Furthermore, a moiety interacting with the detectable tag in the complex may be present on the second polynucleotide.

Preferred forms of detectable tags, especially if remote from the target binding region of the labeled probe polynucleotide, should have little or no effect on the strength of base pairing between the labeled probe polynucleotide and either the second polynucleotide or the target nucleotide sequence, as evidenced (for testing purposes) by little or no diminution of the reagent complex melting temperature and, more importantly, by negligible effects on the hybridization reaction between the target nucleotide sequence and the labeled probe polynucleotide.

The second polynucleotide (which can be DNA or RNA) includes a pairing segment bound in the reagent complex to the labeled probe polynucleotide by complementary base pairing. The length of such pairing segment corresponds to the length of the second polynucleotide binding region of the probe. While such pairing is normally confined to a portion of the target binding region, some limited number of base pairs outside of the target binding region (e.g., up to 15 such nucleotide pairs) is permitted, but not preferred. The effect of such an overhang or residual binding region corresponds to the effect of the RBR discussed in relation to FIG. 1G of U.S. Ser. No. 607,885. The pairing between the second polynucleotide and the labeled probe polynucleotide can be perfect or can include a limited number of mismatches. The second polynucleotide can also be bound in the inverse reagent complex via multiple pairing segments each to a portion of a unique target binding region of the labeled probe polynucleotide. Such second polynucleotide would be fully displaced either by multiple target nucleotide sequences of the sample, or by one or more sample target nucleotide sequences and one or more selected nucleotide sequences of a reagent polynucleotide in a manner analogous to that described in U.S. Ser. No. 777,796 of Fritsch and Collins, filed Sept. 19, 1985, the disclosure of which is incorporated herein by reference. Additionally, the selected polynucleotide may bind to the second polynucleotide so as to displace a pairing segment from a portion of a target binding region in an inverse fashion relative to that described in U.S. Ser. No. 777,796.

In addition to the pairing segment, the second polynucleotide can either contain a moiety for immobilization or can be immobilized to a solid support in the reagent complex as formed. Such moiety for immobilization is exemplified by biotin, in which case the post-displacement separation would involve immobilized avidin, streptavidin or anti-biotin antibody. "Immobilizable" as used herein further encompasses susceptibility to any method leading to physical separation of labeled probe polynucleotides from which second polynucleotide has been displaced from intact reagent complex (e.g. size separation, phase separation, gel electrophoresis, etc.). In the case of second polynucleotides immobilized to a solid support in the inverse reagent complex, covalent linkages (including those prepared by ligation as described in U.S. Ser. No. 729,700 of Brown, et al., filed May 2, 1985) are preferred.

FIG. 1A shows an embodiment of inverse reagent complex IRC according to the present invention with an immobilized second polynucleotide SP. The second polynucleotide SP has one end attached to a support SU and has a pairing segment PS at the opposite end. The labeled probe polynucleotide LP has a detectable tag T at one end and a target binding region TBR including about half of the overall length of the labeled probe polynucleotide, including the end opposite tag T. The end half (PS') of TBR is bound by complementary base pairing to pairing segment PS of immobilized second polynucleotide SP; the interior half of TBR is single-stranded and is designated the initial binding region IBR.

Figure 1B:
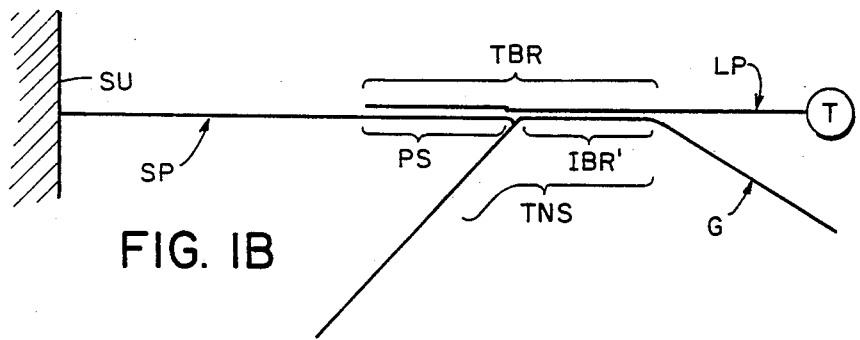

FIG. 1B shows the inverse reagent complex IRC after a sample polynucleotide G having the target nucleotide sequence TNS has hybridized to the initial binding region IBR. At this point, the portion IBR' complementary to IBR forms a double-stranded portion IBR/IBR' joining sample polynucleotide G to labeled probe polynucleotide LP. Since the labeled probe polynucleotide LP remains bound to segment PS of SP, all three stands remain attached to support SU.

Figure 1C:
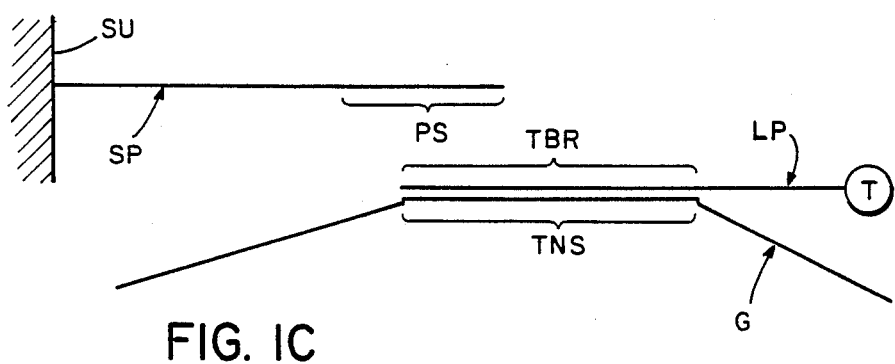

Strand migration may now occur in which segment PS and the remainder of TNS zip and unzip within the end half of TBR. As discussed in U.S. Ser. No. 607,885, such phenomenon is very rapid, and in a matter of minutes or less, the strand that can be completely displaced (in this case SP) is displaced. As shown in FIG. 1C, the target nucleotide sequence TNS has now completely displaced pairing segment PS of second polynucleotide SP from the target binding region TBR of the labeled probe polynucleotide LP. The hybrid G/LP (which includes tag T) can now migrate away from support SU and be separated therefrom in a liquid phase. All intact inverse reagent complexes (which have not been contacted by target nucleotide sequence TNS and thus remain as shown in FIG. 1A) should remain on support SU. Thus the tags T detected directly or indirectly in the separated liquid phase give a qualitative and a quantitative measure of the target nucleotide sequence TNS in the sample.

Departures from the geometry shown in FIGS. 1A–1C within the scope of the present invention can be understood by reference to various Figures of earlier applications on strand displacement assays. In FIG. 1A hereof, the pairing segment PS binds only to a portion of TBR; there is no residual binding region of labeled probe polynucleotide bound to PS but not part of TBR. By analogy to FIG. 1G and the accompanying description (and Example 13) of U.S. Ser. No. 607,885, some number of such nucleotides are permissible; but, in general, such a residual binding region is preferably no greater than 15 nucleotides in length. If such a residual binding region is present, then at the stage of complete displacement shown in FIG. 1C (TNS fully hybridized with TBR) such residual binding region of LP could still be bound to PS. The reaction conditions (particularly temperature and salt concentration) should be chosen, or adjusted at the end of the reaction, to conditions at which labeled probe polynucleotides LP bound only by the residual binding region melt off the pairing segment PS.

In FIGS. 1A–1C, the second polynucleotide SP is immobilized to a support SU in the reagent complex IRC as formed. In other embodiments, the end of the second polynucleotide opposite to PS has a moiety (e.g., biotin as in a poly-bio-dU tail) immobilizable by immobilized avidin or streptavidin. In such cases, the displacement is preferably conducted in solution and, thereafter, the reaction mixture is contacted with immobilized avidin or streptavidin. Such step immobilizes intact reagent complexes IRC and displaced second polynucleotides SP, leaving sample strand/labeled probe hybrids (G/LP) in solution for subsequent direct or indirect detection. By analogy to U.S. Ser. No. 729,501 of Unger, et al., filed May 2, 1985, a homopolynucleotide tail (e.g., poly-dC) can be present on the end of SP opposite the pairing segment PS; in such case the post-displacement immobilization step would employ an immobilized complementary homopolynucleotide (e.g., oligo-dG-cellulose to immobilize the poly-dC tails of SP).

In all such cases where the labeled probe polynucleotide LP/sample polynucleotide G hybrid are in a liquid phase for subsequent detection, intermediate treatments can be conducted to obtain further information (such as restriction fragment size or sequence information) about sample polynucleotide G. Thus, the liquid phase may be subjected to gel electrophoresis (including the denaturing gel electrophoresis of Fisher, S. G. and Lerman, L. S. (1983) Proc. Natl. Acad. Sci USA 72, 989–993; Myers, R. M. et al. (1985) Nature 313: 495–498) restriction endonuclease treatment or S1 nuclease digestion or ribonuclease digestion (see Myers, R. M. et al. (1985) Science 230: 1242–1246) in order to develop information beyond merely the number of target nucleotide sequences TNS.

FIG. 2A illustrates an inverse reagent complex construct IRCC, having a single polynucleotide strand. This strand includes a pairing segment PS near one end and a target binding region TBR adjacent to the opposite end, which opposite end also bears a detectable tag T. The pairing segment is bound by complementary base pairing to the half of the target binding region nearest to the tag T, leaving the interior half of the target binding region TBR single-stranded as an initial binding region IBR.

FIG. 2B shows such an inverse reagent complex construct IRCC which has been contacted by a sample polynucleotide strand G containing the target nucleotide sequence TNS. Target nucleotide sequence TNS has bound to all of the target binding region TBR, displacing pairing segment PS. Pairing segment PS, in FIG. 2B, is in single-standard form, but remains attached to segment TBR and tag T by the covalent phosphate/sugar backbone (although other stable attachment could be used). An interior portion of segment PS is indicated as CS'.

FIG. 2C illustrates the hybrid of FIG. 2B subsequently bound by an immobilized capture polynucleotide CP which contains a portion CS complementary to CS'. Capture polynucleotide (CP) will capture the hybrid shown in FIG. 2B, but not the intact inverse reagent complex IRC shown in FIG. 2A. Intermediate structures similar to those shown in FIG. 2E of the copending application U.S. Ser. No. 809,971 filed herewith (and discussed in connection therewith) are also possible in many cases. As with the embodiments discussed there, it may be desirable in using the inverse reagent complexes IRC shown in FIG. 2A, to employ proportions, orders of addition or other parameters either to avoid or fully resolve any such second intermediate structures (CP/TNS/IRC) as may form.

Modifications can be made in the inverse reagent complex shown in FIG. 2A whereby the inverse reagent complex is initially immobilized. Initial immobilization of the inverse reagent complex of FIG. 1A requires an immobilized third polynucleotide would be provided having a binding segment complementary to and bound to a portion of TBR other than the portion of TBR bound to PS: either (1) BS would be bound to a portion of the IBR segment shown in FIG. 2A or (2) the TBR region would extend to the right (as well as in IBR to the left) of the PS' portion and BS would be bound to all or a portion of TBR to the right of PS'. Displacement of such third polynucleotide would release reagent complex from the support.

In considering the captured structure shown in FIG. 2C, the tag T can be detected on the solid phase or can be introduced into a new liquid phase, after the liquid phase containing intact reagent complexes has been removed. Further discussion of suitable capturing steps and of techniques for redissolving the tag before detection is contained in a copending application filed herewith entitled, "METHOD AND KIT INVOLVING DISPLACEMENT AND REHYBRIDIZATION OF LABELED POLYNUCLEOTIDE", U.S. Ser. No. 809,971, the disclosure of which is incorporated herein by reference.

EXAMPLES 1-2

Construction of inverse reagent complex, model polynucleotide analyte and capturer I. Inverse displacement complex: Displacement complexes were prepared from a nucleic acid construct made by the methods described in U.S. Ser. No. 729,504 (Fritsch and Collins). The pMLC12/13deltaM7IVRTL construct, described and illustrated in FIG. 4D of that application, contains fragments from the human albumin gene cloned as inverted repeats in an M13 origin plasmid. These fragments were cloned into the center of a small inverted repeat derived from the M13mp7 polylinker. Single stranded forms of this construct fold up into a stem loop structure. Cleavage of the Mp7 polylinker with a restriction enzyme releases the stem-loop structure from the single stranded vector backbone. This insert can be used directly as a (1.6 kb nucleotide) covalent displacement complex with a 0.5 kb Bgl II-Hinc II albumin fragment as the signal strand, and a 1 kb Bgl II-Pvu II albumin fragment nucleotide target binding region (such nucleotide numbers are approximate). In single stranded complexes the target binding region is located 22 nucleotides from the 5' end and the signal strand 41 nucleotides from the 3' end.

pMLC12/13deltaM7IVRTL contains an additional inverted repeat (IVRTL) located at the inside edge of the signal strand, which forms a 52 nucleotide (26 base pair, see FIG. ID of U.S. Ser. No. 729,504) hairpin containing a double-stranded Eco RI cleavage site in single stranded forms of this construct. Cleavage at both the Bam HI site in the mp7 polylinker and at the IRTL Eco RI site results in the formation of a displacement complex in which the signal strand and target strand are held together only by base pairing. We will distinguish between these two forms of the construct in which the IVRTL hairpin is or is not cleaved by Eco RI by referring to them as the covalent complex and the non-covalent complex, respectively.

p66b was constructed by gel-isolating the double-stranded PvuII fragment containing the sequence for the entire displacement complex from pMLC12/13deltaM7IVRTL and ligating it to the gel-isolated Pvu II backbone of the M13 origin plasmid pUC119. Single stranded forms of this construct were produced as previously described for pMLC12/13deltaM7IVRTL, except that the DNA was transformed into the E. coli host strain MV1193 obtained from Dr. Michael Volkert (JM 101 del(srIR-recA) 306::Tn10), and superinfections are routinely done with bacteriophage M13K107. The resulting displacement complexes are identical to those produced by pMLC12/13deltaM7IVRTL; this method is preferred only due to higher yields of the displacement complex.

Inverse reagent complex used in Examples 1 and 2 results from labeling of the 5' end of p66b. II. Model Analyte: Model analyte was constructed by gel purifying a 2 kb Hind II-Eco RI fragment from a plasmid, pA11A1b, which contains the entire cDNA sequence of human albumin. The HindIII site is the HindIII site in the 3' end of the albumin cDNA. The EcoRI site is present in adjacent vector sequences. The vector sequences present on the HindIII EcoRI fragment have no bearing on the following examples. The Hind III-EcoRi fragment was ligated into Hind III-EcoRI digested M13mp8 to give mp8a11A1b. Single stranded DNA was purified from phage containing this construct, and was partially digested with Hae III to linearize these model analytes. There are no HaeIII sites within the albumin cDNA sequence. mp8.A11A1b template DNA is complementary to the target binding region of p66b displacement complexes.

III. Model Capturer: mp19.AlbTaqPst was constructed by ligating a 280 base pair PstI-TaqI segment isolated from a 350 base pair BglII-PstI fragment of human albumin CDNA into AccI/PstI digested mp19 Rf DNA. mp7delta.a1bXba construct 1+ was made by digesting mp19.A1bTaqPst Fr DNA with Xba I, and end filling gel purifying the resulting 300 base pair fragment, and ligating it to the 6800 base pair gel purified Pvu II vector backbone fragment of mp7. One of the two resulting phage isolates containing single stranded albumin DNA complementary to the labeled polynucleotides of p66b displacement complexes is labeled 1+. Construct mp7deltaAlbXbal+ differs from mpl9.AlbTaqPst used in the copending application on capture in that a portion of the lac gene and all polylinker cloning sequences are deleted from the mp7delta backbone, and in that the albumin insert is complementary to a more interior portion of the pairing segment.

c4. Biotinylation of mp7AlbXbal+ DNA using Vector Laboratories Photoprobe ™ Biotin.

The capturing strand mp7deltaALBXbal+ was biotinylated using the commercially obtained Photoprobe Biotin (Vector Laboratories) essentially as described by the manufacturer and repeated below.

Photoprobe ™ biotin (a 500 ug) was resuspended in 500 microliter water as recommended by the manufacturer and stored in the dark at −20° C. 10 micrograms of template DNA from the clone mp7deltaAlbTaqXbal+ was ethanol precipitated and resuspended in 10 microliter H$_2$O. The DNA was mixed with 10 microliter Photoprobe biotin solution under a safelight, sealed in a glass microcapillary pipette and irradiated by a sunlamp (GE infrared lamp 2JOR40/1) for 20 or 30 minutes in separate reactions. The sample was kept in an ice-H$_2$O bath during the entire irradiation procedure. After irradiation, the sample was removed from the capillary, diluted with 100 microliters of 0.1M Tris-HCl, pH 8.0, extracted twice with 2-butanol and precipitated following addition of 1/10 volume 3M Na Acetate and 2 volumes of ethanol. The precipitated sample was resuspended in 10 microliters 011 mM EDTA, pH 8.0.

Successful reaction was monitored by taking an aliquot of the biotinylated DNA and hybridizing a 32-P labeled oligonucleotide (cALB 32-mer) complementary to a 32 base segment of the capture strand. One-half of the sample (control) was then electrophoresed directly on an agarose gel. The other half was mixed with 10 microliter of streptavidin latex beads supplied from Pandex Laboratories in 0.2M NaCl, 20 mM Tris-HCl, pH 8.0, 0.1% NP-40 for 10–20 minutes at room temperature. After the binding step, the beads were removed from the solution by centrifugation (2 minutes, Eppendorf centrifuge) and the combined solution phases were electrophoresed in a parallel lane to the control sample. Following electrophoresis and autoradiography, the results indicated that nearly all the 32-P labeled oligonucleotide sample that was hybridized to the mp7deltaAlbXbal+ DNA was removed from the sample that was exposed to the streptavidin agarose, indicating that the majority of template DNAs (capture strands) had a least one biotin group attached.

EXAMPLE 1

Large scale displacement and capture with trapping on streptavidin agarose.

The Bam p66b displacement complex was labeled to a specific activity of about 106 cpm/pm by ligating a 32p-kinased oligonucleotide to the 5' end of the complex with the use of a 21 base splint. 10 pm of the kinased 16mer (indicated below by the asterisk), 10 pm of splint, and 1 pm of p66b Bam (underlined below) were incubated together at 22° C. for 15 minutes in 10 ul of 1× ligase buffer; 1 ul of ligase was added and the reaction incubated for an additional 30 minutes. The three molecules form the joint diagrammed below.

```
*CGAAGCTTGGATCCGCGATCCGTCAGCTT....p66b
      GAACCTAGGCGCTAGGCAGT (SPLINT)
```

The four reactions outlined in Table 1 were set up in a total volume of 50 ul of hybridization buffer (0.3M NaCl, 0.1M Tris HCl, pH8.0, and 10 mM EDTA) and incubated for 30 minutes at 65° C. Hae III cut mp8AllAlb and biotinylated mp7deltaAlbXbal+ DNA were used as analyte and capturer, respectively. 25 ul of each reaction was then analyzed by gel electrophoresis and 25 ul by binding to streptavidin agarose as follows. 100 ul packed volume of streptavidin agarose was washed twice in 500 ul binding buffer in a 5 ml Sarstedt tube rotated end over end for 15 minutes, and pelleted by centrifugation. The 25 ul reaction aliquots were diluted to a total of 500 ul binding buffer, and incubated, rotating as above, for 15 minutes. The sample was transferred to an Eppendorf tube for centrifugation, the supernatant saved, and the pellet rewashed as above, once at room temperature for 15 minutes, then twice at 65° C. for 15 minutes, then for 60 minutes at room temperature and finally for 15 minutes at room temperature with TE. The final pellet and all supernatants were counted. Data showing the cpm bound to agarose after each rinse are given in Table 1. These results show that binding of complex to the support is dependent upon the presence of capturer and analyte, and upon the amount of analyte present.

Gel analysis of the same reactions indicated that there is less than 0.05% non-specific capturing in these reactions. Specific capturing was more efficiently analyzed by gel separation, in that the presence of analyte resulted in capturing of approximately 80% and 20% of the complex in reactions 3 and 4, respectively.

TABLE 1

| REACTION | pm COMPLEX | pm ANALYTE | pm CAPTURER |
|---|---|---|---|
| 1 | 0.10 | 0 | 0 |
| 2 | 0.10 | 0 | 0.16 |
| 3 | 0.10 | 0.05 | 0.16 |
| 4 | 0.10 | 0.01 | 0.16 |

| | CPM BOUND TO SUPPORT | | | |
|---|---|---|---|---|
| REACTION | 1 | 2 | 3 | 4 |
| TOTAL: | 46435 | 42590 | 49423 | 41889 |
| RINSE 1: | 12915 | 10150 | 274308 | 15394 |
| RINSE 2: | 5254 | 3217 | 22982 | 10109 |
| RINSE 3: | 3911 | 2032 | 19978 | 7806 |
| RINSE 4: | 3500 | 1594 | 16261 | 6238 |
| RINSE 5: | 2203 | 1458 | 13780 | 5391 |
| RINSE 6: | 1482 | 1227 | 12351 | 4436 |
| FINAL: | 813 | 1044 | 10628 | 3658 |
| % BOUND: | 1.7 | 2.5 | 26.3 | 8.7 |

EXAMPLE 2

Prehybridization of complex and analyte, followed by capturing and trapping

Two additional reactions were done using the Bam p66b complex described in Example 1. In these reactions, 0.1 pm complex alone (reaction 1) or 0.1 pm complex and 0.05 pm Hae III cut mp8AllAlb analyte (reaction 2) were incubated in 50 ul of hybridization buffer for 30 minutes at 65° C. 0.16 pm of biotinylated mp7delta.AlbXbal+ was then added to both reactions, which were then divided and treated as in Example 1, except that all rinses were at room temperature with binding buffer. By gel analysis, less than 0.05% nonspecific capturing, and approximately 40% specific capturing was observed. The results of analysis on streptavidin agarose (Table 2) indicate that capturing and trapping occur with approximately equal efficiencies whether capture DNA is added after (as in this Example 2) or is present during (as in Example 1) the analyte-dependent displacement reaction.

TABLE 2

| REACTION | CPM BOUND TO SUPPORT | |
| --- | --- | --- |
| | 1 | 2 |
| TOTAL: | 57860 | 55210 |
| RINSE 1: | 10364 | 18538 |
| RINSE 2: | 4360 | 14321 |
| RINSE 3: | 3046 | 11983 |
| RINSE 4: | 3035 | 9745 |
| RINSE 5: | 1781 | 8897 |
| FINAL: | 1124 | 7428 |
| % BOUND: | 1.9 | 13.5 |

What I claim is:

1. A method for determining the presence and amount of a predetermined target nucleotide sequence in the nucleic acid of a biological sample which comprises the steps:
   (a) providing a reagent complex formed by a single nucleic acid strand comprising (i) labeled probe polynucleotide which is capable of base pair binding via hydrogen bonds of purine/pyrimidine bases to the target nucleotide sequence, and (ii) a second polynucleotide which is covalently attached by phosphate-sugar backbone to the labeled polynucleotide and which is bound by base pair binding via hydrogen bonds of purine/pyrimidine base pairs to the labeled probe polynucleotide in a region of the labeled probe polynucleotide at least partially coextensive with the region in which the labeled probe polynucleotide is capable of binding to the target nucleotide sequence;
   (b) contacting the reagent complex with a sample under conditions in which the target nucleotide sequence, if present, binds to the labeled probe polynucleotide and displaces second polynucleotide from the labeled probed polynucleotide;
   (c) immobilizing said displaced second polynucleotide by binding to an immobilized third polynucleotide complementary to a portion of the displaced second polynucleotide and capable of binding by hybridization to a portion of said displaced second polynucleotide, thereby separating labeled probe polynucleotides from which second polynucleotide has been displaced from intact reagent complexes; and
   (d) measuring the resulting immobilized labeled probe polynucleotide/target sequence hybrids.

2. The method of claim 1 wherein a portion of the second polynucleotide located on said nucleic acid strand adjacent to one end thereof is bound by complementary base pair binding in the complex to a portion of the labeled probe polynucleotide located on said nucleic acid strand adjacent to the other end thereof.

3. The method of claim 2 wherein a detectable tag is on the other end of the nucleic acid strand.

4. A method for determining the presence and amount of a predetermined target nucleotide sequence in the nucleic acid of a biological sample which comprises the steps:
   (a) providing a reagent complex formed by a single nucleic acid strand comprising (i) labeled probe polynucleotide which is capable of base pair binding via hydrogen bonds of purine/pyrimidine bases to the target neucleotide sequence, and (ii) a second polynucleotide which is stably joined to the labeled polynucleotide and which is bound by base pair binding via hydrogen bonds of purine/pyrimidine base pairs to the labeled probe polynucleotide in a region of the labeled probe polynucleotide at least partially coextensive with the region in which the labeled probe polynucleotide is capable of binding to the target nucleotide sequence;
   (b) contacting the reagent complex with a sample under conditions in which the target nucleotide sequence, if present, binds to the labeled probe polynucleotide and displaces second polynucleotide from the labeled probe polynucleotide;
   (c) immobilizing said displaced second polynucleotide by binding to an immobilized third polynucleotide complementary to a portion of the displaced second polynucleotide and capable of binding by hybridization to a portion of said displaced second polynucleotide, thereby separating labeled probe polynucleotides from which second polynucleotide has been displaced from intact reagent complexes; and
   (d) measuring the resulting immobilized labeled probe polynucleotide/target sequence hybrids.

5. The method of claim 4 wherein the labeled probe polynucleotide contains a detectable tag.

* * * * *